United States Patent [19]
Caufield et al.

[11] Patent Number: 5,286,730
[45] Date of Patent: Feb. 15, 1994

[54] METHOD OF TREATING IMMUNOINFLAMMATORY DISEASE

[75] Inventors: Craig E. Caufield, Plainsboro, N.J.; John H. Musser, Alameda, Calif.; Surendra N. Sehgal, Princeton, N.J.

[73] Assignee: American Home Products Corporation, New York, N.Y.

[21] Appl. No.: 931,242

[22] Filed: Aug. 17, 1992

Related U.S. Application Data

[63] Continuation-in-part of Ser. No. 761,120, Sep. 17, 1991, abandoned.

[51] Int. Cl.⁵ .................... A61K 35/00; A61K 31/395
[52] U.S. Cl. .................................................. 514/291
[58] Field of Search ..................................... 514/291

[56] References Cited

U.S. PATENT DOCUMENTS

| | | | |
|---|---|---|---|
| 3,929,992 | 12/1975 | Sehgal et al. | 424/122 |
| 4,023,264 | 6/1991 | Caufield et al. | 549/90 |
| 4,996,193 | 2/1991 | Hewitt et al. | 514/11 |
| 5,023,263 | 6/1991 | Von Burg et al. | 519/291 |
| 5,078,999 | 1/1992 | Warner et al. | 424/122 |
| 5,080,899 | 1/1992 | Sturm et al. | 514/291 |

FOREIGN PATENT DOCUMENTS 0315978 5/1988 European Pat. Off.

OTHER PUBLICATIONS

Mark S. Fradin, et al., J. Am. Acad. Dermatol. 23:1265 (1990).
C. P. Eng. et al., Transplant. Proc. 23:868 (1991).
J. E. Kay, Immunology 72:544 (1991).
C. N. Ellis, J. Am. Med. Assoc. 256:3110 (1986).
C. N. Ellis, N.E. Jour Med. 324:277 (1991).
R. R. Martel, Can. J. Physiol. Pharmacol. 55, 48 (1977).
M. J. Staruch, FASEB 3, 3411 (1989).
R. Morris, Med. Sci. Res. 17:877 (1989).
J. G. Meingassner, J. Invest. Dermatol. 98: 851 (1992).

*Primary Examiner*—Nathan M. Nutter
*Attorney, Agent, or Firm*—Arnold S. Milowsky

[57] ABSTRACT

This invention provides a method of treating immunionflammatory skin disease in a mammal in need thereof which comprises administering an antiimmunoinflammatory amount of rapamycin, alone or in combination with cyclosporin A, orally, parenterally, intranasally, intrabronchially, topically, transdermally, or rectally. As such, rapamycin, alone or in combination with cyclosporin A, is useful in treating skin diseases such as psoriasis, atopic dermatitis, contact dermatitis, eczematous dermatitis, seborrheic dermatitis, Lichen planus, Pemphigus, bulus pemphigoid, Epidermolysis bullosa, urticaria, angioedemas, vasculitides, erythemas, cutaneous eosinphilias, and the like.

4 Claims, No Drawings

METHOD OF TREATING IMMUNOINFLAMMATORY DISEASE

CROSS REFERENCE TO RELATED APPLICATION

This application is a continuation in part of Ser. No. 07/761,120, filed Sept. 17, 1991 and now abandoned

BACKGROUND OF THE INVENTION

Skin diseases such as contact hypersensitivity, atopic dermatitis, and psoriasis are characterized by hyperproliferative and inflammatory skin disorders. A large population suffers from these disorders, psoriasis; for example, afflicts approximately 2% of the population in Western countries [Ziboh, V. A. Psoriasis: Hyperproliferative/Inflammatory skin disorder, Drug Development Research 13: 137-146, (1988)]. Human skin diseases like psoriasis are characterized by histopathologically distinct patterns of infiltration by T cells, B cells, monocytes and granulocytes. These leukocyte cell infiltrations are the consequence of expression of intercellular adhesion molecules and release of cytokine and chemotactic factors by nonhematopoietically derived cells (e.g. keratinocytes) of the skin which in turn augment hyperplasia.

Current treatment of immunologically mediated skin disorders involves the use of antiinflammatory agents such as glucocorticoids and antiproliferative agents such as methotrexate, 5-fluorouracil, and retinoids. Recently, use of the immunosuppressive agent cyclosporin A has been reported to give clinical improvement of psoraisis. [Ellis, J. Am. Med. Assoc. 256: 3110-3116, (1986)]. However, its usefulness in psoriasis is limited due to high incidence of nephrotoxicity [Ellis, New England J. Med. 324: 277-84, (1991)], and the observation of relapse after cessation of the treatment with cyclosporin A [Griffiths, J. Am. Acad. Dermatol. 23: 1242-1247, (1990)].

Rapamycin, a macrocyclic triene antibiotic produced by Streptomyces hygroscopicus [U.S. Pat. No. 3,929,992] has been shown to prevent the formation of humoral (IgE-like) antibodies in response to an albumin allergic challenge [Martel, R., Can. J. Physiol. Pharm. 55: 48 (1977)], inhibit murine T-cell activation [Staruch, M., FASEB 3: 3411 (1989)], and prolong survival time of organ grafts in histoincompatible rodents [Morris, R., Med. Sci. Res. 17: 877 (1989)].

DESCRIPTION OF THE INVENTION

This invention provides a method of treating immunoinflammatory skin disease in a mammal in need thereof which comprises administering an antiimmunoinflammatory amount of rapamycin orally, parenterally, intranasally, intrabronchially, topically, transdermally, or rectally. In particular, rapamycin is useful in providing symptomatic relief of, preventing the progression of, or eradicating inflammatory skin disease. As such, rapamycin is useful in treating skin diseases such as psoriasis, atopic dermatitis, contact dermatitis, eczematous dermatitis, seborrheic dermatitis, Lichen planus, Pemphigus, bulus pemphigoid, Epidermolysis bullosa, urticaria, angioedemas, vasculitides, erythemas, cutaneous eosinphilias, and the like.

The effect of rapamycin on skin disease was established in two in vivo standard animal pharmacological test procedures emulating skin immunoinflammatory diseases observed in mammals. The procedures used and results obtained are described below.

The first in vivo standard pharmacological test procedure measured the effect of rapamycin on dermal inflammation, as measured by the prevention of tetradecanoylphorbol acetate (TPA) induced ear edema in Webster mice. Cyclophosphamide, cyclosporin (CsA), indomethacin, and BW755C also were evaluated for the purpose of comparison. The following briefly describes the procedure used.

Female Swiss Webster mice (Buckshire; 8 weeks old) were divided into groups of six. Tetradecanoylphorbol acetate (TPA) were dissolved in acetone at concentrations of 200 µg/ml. Each mouse received 4 µg/ear of TPA on the right ear. These suboptimal doses of phlogistics were applied by an automatic pipette in 10 µl volumes to both the inner and outer surfaces of the ear. The left (control) received acetone or vehicle. Drugs were applied topically in acetone and in some cases 95% ethanol was used to solubilize the drug prior to dilution with acetone. Topical drug regimen was as follows: drugs were given 30 min. after treatment with TPA. Edema measurements were taken with an Oditest calipers. The thickness of the right and left ears were usually measured in units of 0.01 mm 4 h after TPA application. Ear edema was calculated by subtracting the thickness of the left ear (vehicle control) from right ear (treated ear).

The results obtained in the TPA induced ear edema standard pharmacological test procedure are shown in the following table.

| Treatment Group | Dose (mg/ear) | Mean Edema ($mm^{-2}$ ± SEM) | Percent Change |
|---|---|---|---|
| Control | | 28.3 ± 1.1 | — |
| Rapamycin | 0.25 | 17.8 ± 4.1 | −37.1* |
| Rapamycin | 1.0 | 12.0 ± 2.5 | −57.6* |
| Cyclophosphamide | 0.25 | 16.5 ± 3.1 | −41.7* |
| Cyclophosphamide | 1.0 | 15.0 ± 2.4 | −47.0 |
| Cyclosporin A | 0.25 | 23.8 ± 2.0 | −15.9 |
| Cyclosporin A | 1.0 | 26.0 ± 1.3 | −7.1 |
| Indomethacin | 0.5 | 12.0 ± 2.3 | −57.6* |
| BW755C | 0.5 | 12.0 ± 2.4 | −57.6* |
| BW755C | 1.0 | 12.7 ± 1.4 | −55.1* |

*Statistically significant ($p \leq 0.05$) difference from control mice.

The results of this standard pharmacological test procedure showed that rapamycin significantly ($p \leq 0.05$) prevented an acute inflammatory response following topical TPA administration. Cyclosporin A, an immunosuppressive agent typically compared with rapamycin, prevented the inflammatory response to a much lesser extent.

The second in vivo standard pharmacological test procedure measured the effect of rapamycin on preventing oxazolone-induced contact hypersensitivity of the mouse ear. This test procedure emulates the inflammatory response observed in immunoinflammatory diseases of the skin in mammals. The following briefly describes the procedure used and results obtained. Dexamethasone, and cyclosporin A also were evaluated for the purpose of comparison.

Female, Swiss Webster mice (8 weeks old) were placed into groups of 6 and the abdominal area of each was shaved. The mice were sensitized to oxazolone (4-ethoxymethylene-2-phenyl-oxazol-5-one) by appling 100 µl of a 2% solution in 95% alcohol directly onto the shaved abdomen using an automatic pipette and rubbing the residual oxazolone into the skin with a round wooden stick. Six days after sensitization, each mouse was challenged by applying 20 µl of a 2% oxazolone solution in 95% alcohol to the right ear (10 µl on each side) and 20 µl of alcohol alone to the left ear. Compounds for topical applications were prepared in acetone and administered to the right ear 30 min. after challenge; acetone (vehicle) was applied to the left ear. Compounds for oral administration were suspended in 0.5 ml of 0.5% methyl cellulose and given ten min. prior to challenge. Ear thickness of both ears were measured in (mm $\times 10^{-2}$) at 24 and 48 h after challenge using an Oditest caliper. Edema was calculated by subtracting the left ear thickness from the right ear thickness. Drug effects were determined by calculating the percentage change from control for each time period. The following results were obtained.

| Compound | Dose | Route | Edema (mm × $10^{-2}$ ± SE) | Percent Change |
|---|---|---|---|---|
| Control | | | 34.7 ± 2.9 | |
| Unsensitized | | | 4.2 ± 1.3 | |
| Rapamycin | 20 mg/kg | p.o | 26.8 ± 5.6 | −22.6 |
| Rapamycin | 0.5 mg/ear | topical | 9.7 ± 3.4 | −72.1* |
| Cyclosporin A | 50 mg/kg | p.o. | 27.5 ± 3.9 | −20.7 |
| Cyclosporin A | 1.0 mg/ear | topical | 4.7 ± 1.5 | −86.5* |
| Dexamethasone | 1 mg/kg | p.o. | 25.8 ± 4.2 | −25.5 |
| Dexamethasone | 0.1 mg/ear | topical | 1.2 ± 0.4 | −96.9 |

The results of this in vivo standard pharmacological test procedure emulating immunionflammatory diseases of the skin showed that rapamycin prevented the inflammatory changes in response to oxazalone-induced inflammation. Similar results were observed with dexamethasone and cyclosporin A.

In summary, the results of these standard pharmacological test procedures demonstrate that rapamycin is useful in treating immunoinflammatory skin disorders in a mammal. As such, rapamycin is useful in treating skin diseases such as psoriasis, atopic dermatitis, contact dermatitis, eczematous dermatitis, seborrehic dermatitis, Lichen planus, Pemphigus, bulus pemphigoid, Epidermolysis bullosa, urticaria, angioedemas, vasculitides, erythemas, cutaneous eosinphilias, and the like.

Rapamycin has been shown to act synergistically with cyclosporin A both in vitro and in vivo. For example, Kahan (Transplantation 51: 232(1991)) has shown that rapamycin significantly augmented the inhibitory effects of cyclosporin A upon human peripheral lymphocyte activation by phytohemagglutinin, anti-$CD_3$ monoclonal antibody, and mixed lymphocyte reaction. Cyclosporin A potentiated the effect of rapamycin upon proliferation of IL-2 and IL-6 lymphokine-dependent cell lines. Additionally, the rapamycin/cyclosporin combination exerted immunosuppression of rejection reactions in rats toward heterotopic cardiac allografts, using concentrations at which each was individually ineffective. As such, rapamycin can also be used in combination with cyclosporin A for the treatment of skin diseases such as psoriasis, atopic dermatitis, contact dermatitis, eczematous dermatitis, seborrheic dermatitis, Lichen planus, Pemphigus, bulus pemphigoid, Epidermolysis bullosa, urticaria, angioedemas, vasculitides, erythemas, cutaneous eosinphilias, and the like.

When rapamycin is employed alone or in combination with cyclosporin A in the treatment of immunoinflammatory skin diseases, it can be formulated neat or with a pharmaceutical carrier to a mammal in need thereof. The pharamaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Rapamycin, alone or in combination with cyclosporin A, may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

Rapamycin, alone or in combination with cyclosporin A, may be administered topically as a solution, cream, or lotion by formulation with pharmaceutically acceptable vehicles containing 0.1-5 percent, preferably 2%, of active compound.

The dosage requirements vary with the particular compositions employed, the route of administration, the severity of the symptoms presented and the particular subject being treated. Based on the results obtained in the standard pharmacological test procedure, projected daily dosages of active compound (either being rapamycin alone or in combination with cyclosporin A) would be 0.001-100 mg/kg, preferably between 0.1-50 mg/kg, and more preferably between 0.3-25 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. In general, rapamycin is most desirably administered at a concentration that will generally afford effective results without causing any harmful or deleterious side effects, and can be administered either as a single unit dose, or if desired, the dosage may be divided into convenient subunits administered at suitable times throughout the day.

What is claimed is:

1. A method of treating an immunoinflammatory skin disease selected from the group consisting of psoriasis, atopic dermatitis, contact dermatitis, *eczematous dermatitis, seborrheic dermatitis, Lichen planus, Pemphigus, bulus pemphigoid, Epidermolysis bullosa*, urticaria, angioedema, vasculitide, erythema, and *cutaneous eosinphiliia* in a mammal in need thereof which comprises administering an antiimmunoinflammatory amount of rapamycin orally, parenterally, intranasally, intrabronchially, topically, transdermally, or rectally to said mammal.

2. A method of providing symptomatic relief of, preventing the progression of, or eradicating an immunoinflammatory skin disease selected from the group consisting of psoriasis, atopic dermatitis, contact dermatitis, eczematous dermatitis, *seborrheic dermatitis, Lichen planus, Pemphigus, bulus pemphigoid, Epidermolysis bullosa*, urticaria, angioedema, vasculitide, erythema, and *cutaneous eosinphiliia* in a mammal in need thereof which comprises administering an antiimmunoinflammatory amount of rapamycin orally, parenterally, intranasally, intrabronchially, topically, transdermally, or rectally to said mammal.

3. A method of treating an immunoinflammatory skin disease selected from the group consisting of psoriasis, atopic dermatitis, contact dermatitis, *eczematous dermatitis, seborrheic dermatitis, Lichen planus, Pemphigus, bulus pemphigoid, Epidermolysis bullosa*, urticaria, angioedema, vasculitide, erythema, and *cutaneous esosinphiliia* in a mammal in need thereof which comprises administering an antiimmunoinflammatory amount of a combination of rapamycin and cyclosporin A orally, parenterally, intranasally, intrabronchially, topically, transdermally, or rectally to said mammal.

4. A method of providing symptomatic relief of, preventing the progression of, or eradicating an immunoinflammatory skin disease selected from the group consisting of psoriasis, *atopic dermatitis, contact dermatitis, eczematous dermatitis, seborrheic dermatitis, Lichen planus, Pemphigus, bulus pemphigoid, Epidermolysis bullosa*, urticaria, angioedema, vasculitide, erythema, and *cutaneous eosinphiliia* in a mammal in need thereof which comprises administering an antiimmunoinflammatory amount of a combination of rapamycin and cyclosporin A orally, parenterally, intranasally, intrabronchially, topically, transdermally, or rectally to said mammal.

* * * * *